(12) United States Patent
Ide

(10) Patent No.: US 7,480,397 B2
(45) Date of Patent: Jan. 20, 2009

(54) FINGERPRINT IMAGE READING APPARATUS

(75) Inventor: Hiroyasu Ide, Fussa (JP)

(73) Assignee: Casio Computer Co., Ltd., Tokyo (JP)

( * ) Notice: Subject to any disclaimer, the term of this patent is extended or adjusted under 35 U.S.C. 154(b) by 868 days.

(21) Appl. No.: 10/825,556

(22) Filed: Apr. 14, 2004

(65) Prior Publication Data

US 2004/0208349 A1 Oct. 21, 2004

(30) Foreign Application Priority Data

Apr. 18, 2003 (JP) ............................ 2003-114831
Jun. 4, 2003 (JP) ............................ 2003-159657

(51) Int. Cl.
*G06K 9/00* (2006.01)
(52) U.S. Cl. ..................................... 382/124; 382/115
(58) Field of Classification Search ................. 382/124, 382/115
See application file for complete search history.

(56) References Cited

U.S. PATENT DOCUMENTS

| | | | | |
|---|---|---|---|---|
| 5,177,802 | A * | 1/1993 | Fujimoto et al. | 382/124 |
| 5,475,768 | A * | 12/1995 | Diep et al. | 382/156 |
| 5,539,532 | A * | 7/1996 | Watanabe | 358/443 |
| 5,563,723 | A | 10/1996 | Beaulieu et al. | |
| 6,282,303 | B1 * | 8/2001 | Brownlee | 382/124 |
| 6,324,310 | B1 * | 11/2001 | Brownlee | 382/312 |
| 6,608,941 | B1 * | 8/2003 | Suzuki et al. | 382/272 |
| 6,658,164 | B1 | 12/2003 | Irving et al. | |
| 6,744,910 | B1 * | 6/2004 | McClurg et al. | 382/124 |
| 7,227,978 | B2 * | 6/2007 | Komatsuzaki et al. | 382/124 |
| 2002/0085109 | A1 * | 7/2002 | Nakamura et al. | 348/302 |
| 2003/0016848 | A1 | 1/2003 | Kitajima et al. | |
| 2003/0235329 | A1 * | 12/2003 | Komatsuzaki et al. | 382/124 |
| 2004/0156555 | A1 | 8/2004 | Irving et al. | |

FOREIGN PATENT DOCUMENTS

| | | |
|---|---|---|
| EP | 0 700 195 A2 | 3/1996 |
| JP | 7-264409 A | 10/1995 |
| JP | 9-98255 A | 4/1997 |

(Continued)

OTHER PUBLICATIONS

European Search Report dated Jun. 24, 2008, issued in a counterpart European Application.

*Primary Examiner*—Samir A Ahmed
*Assistant Examiner*—Michael Vanchy, Jr.
(74) *Attorney, Agent, or Firm*—Frishauf, Holtz, Goodman & Chick, P.C.

(57) ABSTRACT

An image reading apparatus which reads a fingerprint image, includes a roller rotatably mounted to the image reading apparatus, a given pattern being printed on part of an outer surface of the roller in a circumferential direction, a line sensor including a plurality of image pickup elements which read a fingerprint image from a finger that touches with the roller as well as the pattern printed on the roller, a generating unit which generates a reference value to each of the image pickup elements corresponding to part of the line sensor, which reads the pattern, based on image data of the pattern, a rotation sensing image extracting unit which extracts a rotation sensing image based on the reference value, and a determination unit which determines capture timing of the fingerprint image based on variations in the rotation sensing image.

9 Claims, 13 Drawing Sheets

FOREIGN PATENT DOCUMENTS

| | | |
|---|---|---|
| JP | 10-79017 A | 3/1998 |
| JP | 11-205554 A | 7/1999 |
| JP | 11-331593 A | 11/1999 |
| JP | 2000-270216 A | 9/2000 |
| JP | 2000-322559 A | 11/2000 |
| JP | 2000-357226 A | 12/2000 |
| JP | 2001-184490 A | 7/2001 |
| JP | 2001184490 A * | 7/2001 |
| JP | 2001-326816 A | 11/2001 |
| JP | 2002-27247 A | 1/2002 |
| JP | 2002-133402 A | 5/2002 |
| JP | 2002-247393 A | 8/2002 |
| KR | 2001-0000534 A | 1/2001 |
| WO | WO 01/11545 A1 | 2/2001 |
| WO | WO 01/33494 A1 | 5/2001 |
| WO | WO 01/67390 A1 | 9/2001 |

* cited by examiner

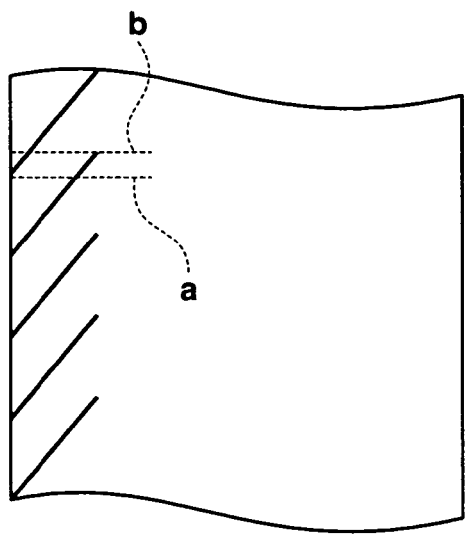
FIG.10
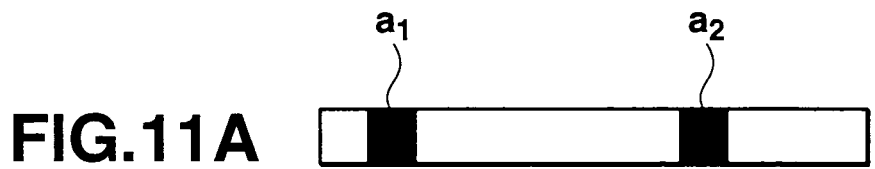
FIG.11A
FIG.11B
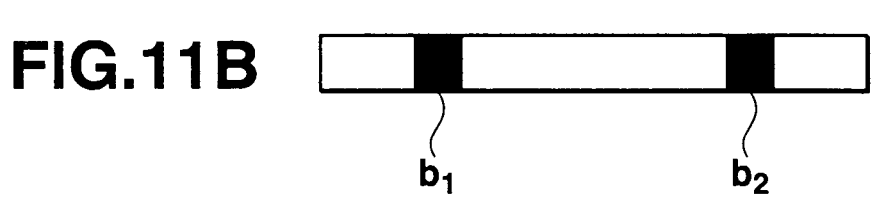

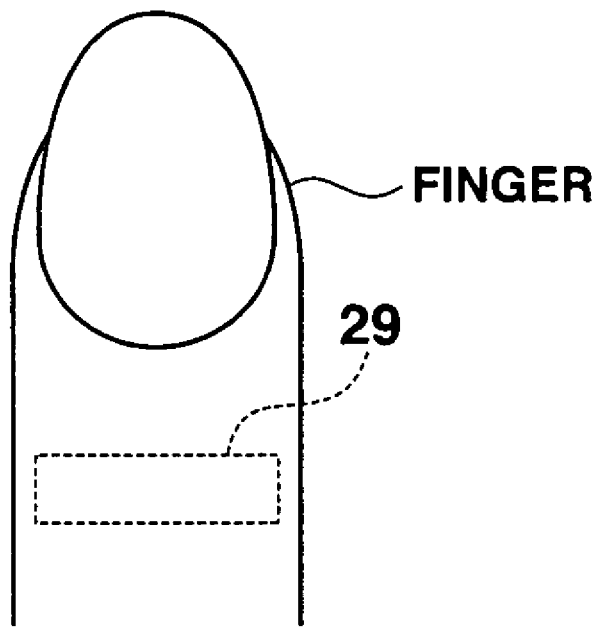
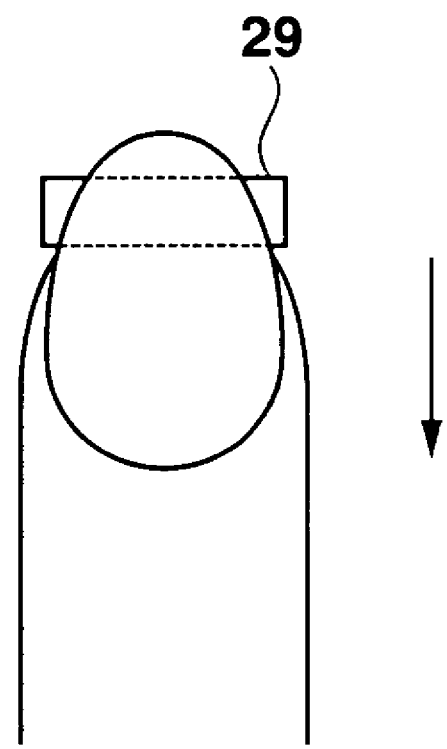
FIG.16A  FIG.16B

FINGERPRINT IMAGE READING APPARATUS

CROSS-REFERENCE TO RELATED APPLICATIONS

This application is based upon and claims the benefit of priority from prior Japanese Patent Applications No. 2003-114831, filed Apr. 18, 2003; and No. 2003-159657, filed Jun. 4, 2003, the entire contents of both of which are incorporated herein by reference.

BACKGROUND OF THE INVENTION

1. Field of the Invention

The present invention relates to an image reading apparatus for reading fingerprint image data.

2. Description of the Related Art

Recently, a fingerprint recognition apparatus (fingerprint image reading apparatus) has been used. This apparatus reads a fingerprint of a person and recognizes it to identify the person.

A fingerprint recognition apparatus using a two-dimensional plane sensor or a one-dimensional line sensor (one-dimensional image pickup device) is proposed. The apparatus using a one-dimensional line sensor has a transparent, flat plate in a fingerprint reading position. A light source for illumination, a rod lens group (a SELFOC lens) and a line sensor are arranged under the transparent, flat plate.

Another fingerprint recognition apparatus using a line sensor is proposed in which the line sensor is incorporated into a hollow, transparent roller. In this apparatus, a user moves his or her finger and presses it on the transparent roller. The line sensor reads a fingerprint image of the pressed finger. A given printing pattern is printed on the outer surface of an end portion of the transparent roller. The line sensor reads the printing pattern as well as the fingerprint image and senses variations in the printing pattern to determine image data reading timing.

In general, an apparatus using a line sensor has to read reference white and black images and prepare adjustment data in advance in order to correct the influence of differences in characteristics between image pickup elements and lens optical systems which configure the line sensor.

To determine a read image by a predetermined reference value is likely to make the operation more unstable because the apparatus using an optical image pickup element is affected by variations in outside light or variations in light source due to a decrease in battery voltage, even though it prepares correction data.

BRIEF SUMMARY OF THE INVENTION

According to an embodiment of the present invention, there is provided an image reading apparatus which reads a fingerprint image, comprising:

a roller rotatably mounted to the image reading apparatus, a given pattern being printed on part of an outer surface of the roller in a circumferential direction;

a line sensor including a plurality of image pickup elements which read a fingerprint image from a finger that touches with the roller as well as the pattern printed on the roller;

a generating unit which generates a reference value to each of the image pickup elements corresponding to part of the line sensor, which reads the pattern, based on image data of the pattern read by the line sensor;

a rotation sensing image extracting unit which extracts a rotation sensing image based on the reference value generated by the generating unit; and a determination unit which determines capture timing of the fingerprint image read by the line sensor based on variations in the rotation sensing image extracted by the rotation sensing image extracting unit.

According to another embodiment of the present invention, there is provided an image processing apparatus comprising:

a line sensor including a plurality of image pickup elements;

a pixel value detecting unit which detects a first pixel value and a second pixel value from each image data including a plurality of pixels output from each the image pickup elements;

a pixel value range detecting unit which detects a pixel value range between the first pixel value and the second pixel value detected by the pixel value detecting unit;

a normalized data generating unit which generates normalized data that indicates a ratio of a pixel value of each of the pixels of the image data to the pixel value range;

a normalized data average calculating unit which calculates an average of the normalized data generated by the normalized data generating unit; and a pixel value correcting unit which corrects a pixel value of each of the pixels of the image data based on the average calculated by the normalized data average calculating unit and the pixel value of each of the pixels.

BRIEF DESCRIPTION OF THE SEVERAL VIEWS OF THE DRAWING

FIG. 10 is a developed, plan view of the printing pattern of the roller in the fingerprint reading apparatus according to the embodiment of the present invention.

FIGS. 11A and 11B are illustrations of variations in the position of a printing portion in a rotation sensing image in the fingerprint reading apparatus according to the embodiment of the present invention.

FIGS. 16A and 16B are illustrations each showing an example of how to move a finger when a fingerprint image is captured by the fingerprint reading apparatus according to the embodiment of the present invention.

DETAILED DESCRIPTION OF THE INVENTION

Figure 1:
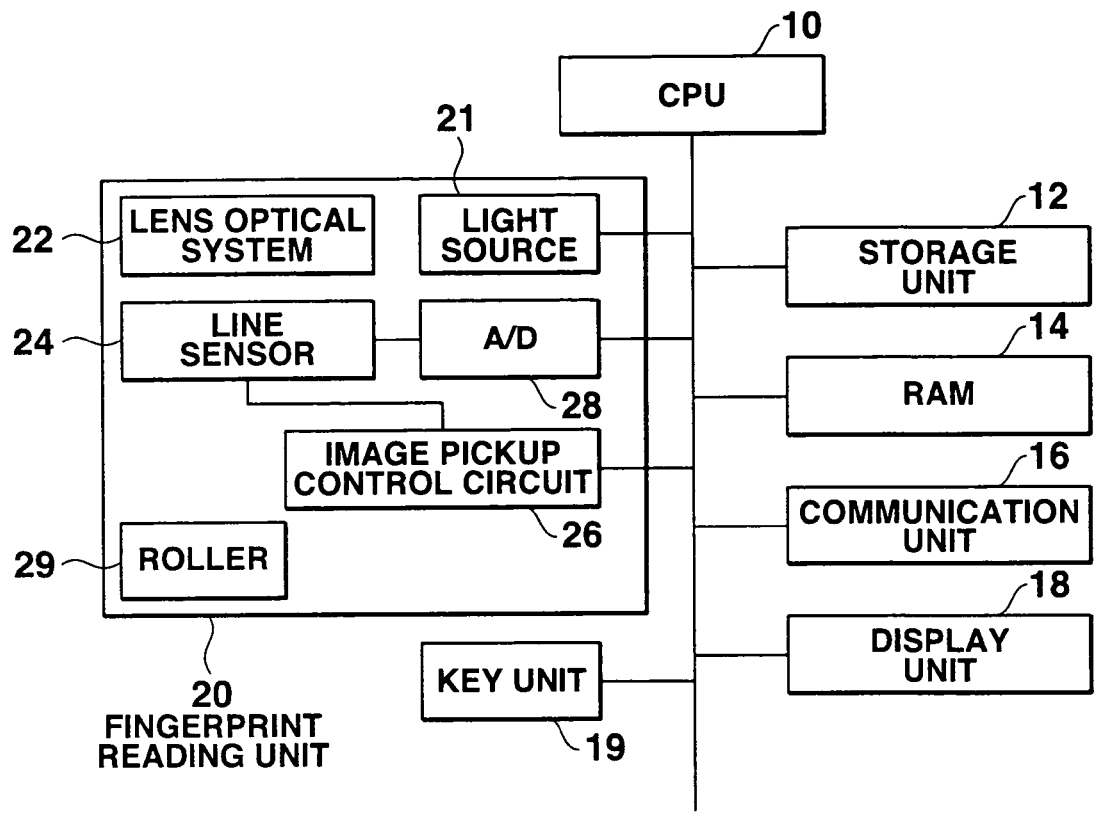
FIG. 1 is a block diagram of an electronic circuit of a mobile phone with a fingerprint reading apparatus according to an embodiment of the present invention.

FIG. 1 is a block diagram of an electronic circuit of a mobile phone with an image reading apparatus according to an embodiment of the present invention.

The mobile phone has a computer which reads programs recorded on a recording medium and whose operation is controlled by the programs. It includes a CPU 10, a storage unit 12, a RAM 14, a communication unit 16, a display unit 18, a key unit 19 and a fingerprint reading unit 20. The CPU 10 is connected to these units through buses. The fingerprint reading unit 20 reads an image of a fingerprint of a user's fingertip as a subject.

The CPU 10 executes programs stored in a program area of the RAM 14 to fulfill various functions. It not only controls the functions of the mobile phone but also controls the fingerprint reading unit 20 to read image data of a fingerprint and performs various processes for the image data.

The storage unit 12 stores programs, data and the like. When the need arises, the programs and data are read out of the unit 12 and stored in the RAM 14.

The RAM 14 stores programs and various data items to which the CPU 10 gains access. More specifically, the RAM 14 stores programs for processing image data of a fingerprint read by the fingerprint reading unit 20 and performing a fingerprint recognition process as well as various programs for controlling the mobile phone. When the unit 20 reads fingerprint image data, the RAM 14 stores the read image data.

The communication unit 16 carries out radio communication for the mobile phone.

The display unit 18 displays various data items when the CPU 10 performs the respective functions.

The key unit 19 is made up of a plurality of keys including numeric keys for inputting telephone numbers and function keys.

Figure 2:
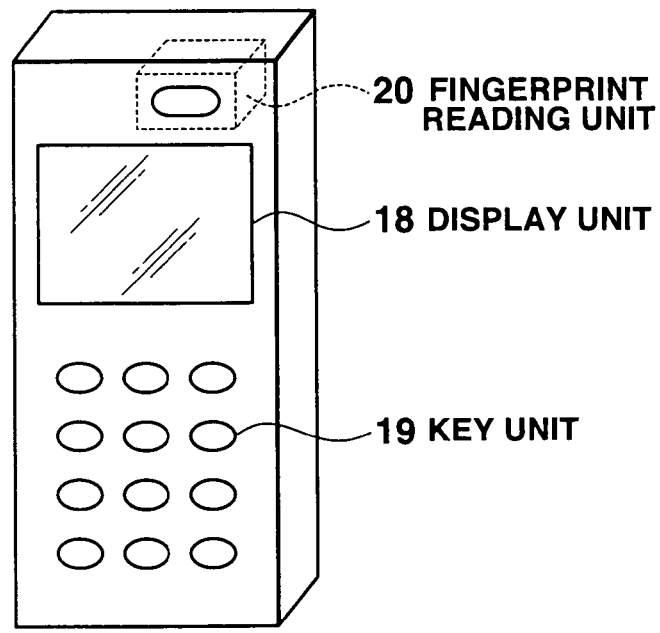
FIG. 2 is an external view of the mobile phone.

The fingerprint reading unit 20 is located on the front top of the mobile phone as shown in FIG. 2 in such a manner that it can easily read image data of a fingerprint. The unit 20 includes a light source 21, a lens optical system (CELFOC lens) 22, a line sensor (one-dimensional image pickup device) 24, an image pickup control circuit 26, an A/D conversion circuit 28 and a transparent, cylindrical roller 29. Part of the outer surface of the roller 29 is exposed to outside from a slit formed in the housing of the mobile phone. A user's finger touches with the exposed part of the roller 29. In order to read a fingerprint of the finger, the roller 29 is rotated while the finger touches with the outer surface of the roller 29 and moves in a give direction (which is perpendicular to the rotation axis of the roller 29). The slit has only to have such a greater width that a user can press his or her finger on the roller 29 and rotate the roller 29. It is thus unnecessary to secure a reading area covering the entire fingerprint, and the area for the fingerprint reading unit 20 (roller 29) occupied in the surface of the housing can be decreased.

In the fingerprint reading unit 20, the light source 21 radiates light. The light is reflected by the finger touching with (contacting) the roller 29 and then condensed on the line sensor 24 through the CELFOC lens 22. The line sensor 24 photoelectrically converts the condensed light into a signal under the control of the image pickup control circuit 26. The A/D conversion circuit 28 converts the signal into image data indicating a fingerprint. The line sensor 24 reads image data periodically, e.g., 20000 times per second. The image data is buffered in the RAM 14. The CPU 10 extracts a printing pattern 30 printed on the roller 29 from the images read by the line sensor 24 as a rotation sensing image. Based on variations in the rotation sensing image, the CPU 10 captures image data suitable for forming a fingerprint image from the periodically read image data and then records it in the RAM 14.

Figure 3:
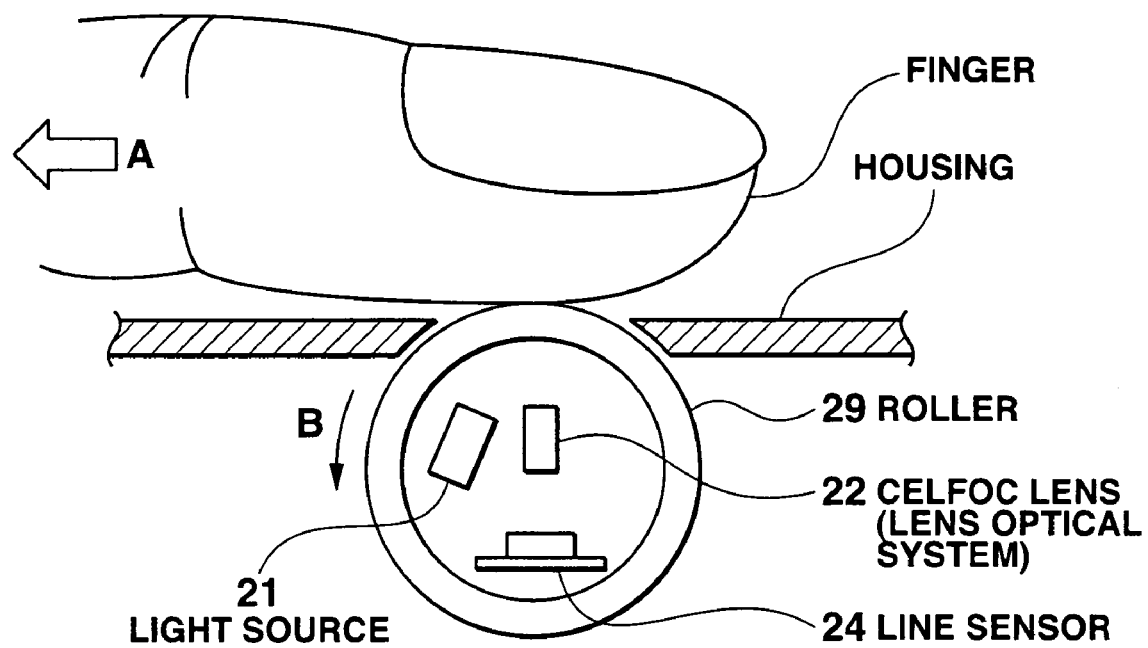
FIG. 3 is a schematic sectional view of a mechanical section of the fingerprint reading apparatus according to the embodiment of the present invention.

FIG. 3 is a schematic sectional view of a mechanical section of the fingerprint reading unit 20.

The housing of the mobile phone has a slit through which part of the outer surface of the roller 29 is exposed. The slit is formed along the rotation axis of the roller 29. The roller 29 is made of transparent materials that transmit light, such as acryl and glass. The roller 29 can rotate with its outer surface partly exposed to outside from the slit. The roller 29 has a hollow containing an image pickup functional unit that is made up of the light source 21, lens optical system (CELFOC lens) 22, and line sensor 24. This unit does not interlock with the rotation of the roller 29.

The CELFOC lens 22 forms on the line sensor 24 an image of a portion of the roller 29 with which a finger touches. The present embodiment is not limited to the CELFOC lens. It can be applied to an image-forming optical system including a rod lens group.

The line sensor 24 is a CCD line sensor, a CMOS line sensor or the like. The line sensor 24 includes a plurality of image pickup elements that are arranged in parallel to the rotation axis of the roller 29. The line sensor 24 has an image pickup range corresponding to the length of the roller 29. It can read an image including the printing pattern 30 that is printed on the roller 29 at one end (or near one end). Since the hollow of the roller 29 includes the image pickup functional unit, the area for the fingerprint reading unit 20 occupied in the housing can be decreased, as can be the volume of the unit 20 therein.

Figure 4:
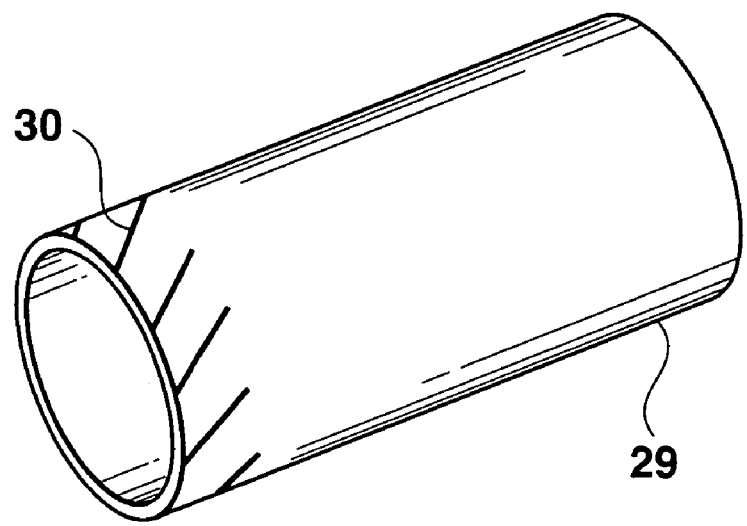
FIG. 4 is a perspective view showing an outward appearance of a roller with a printing pattern in the fingerprint reading apparatus according to the embodiment of the present invention.

FIG. 4 is a perspective view showing an outward appearance of the roller 29.

The printing pattern 30 is formed on the entire circumference of the roller 29. The printing pattern 30 has a plurality of segments that are sloped with respect to the rotation axis of the roller 29 at the same angle. The segments have the same length. If the roller 29 is developed into a plane, the segments are arranged at regular intervals and in parallel to each other. Adjacent segments of the pattern 30 overlap each other in the reading direction (see FIG. 10). Assume that the printing pattern 30 is obtained by forming black segments on a white background. In a correcting data generation process that will be described later, the white background is used as the reference of white images, whereas the segments are used as the reference of black images.

The light source 21 may include an LED, a fluorescent tube, a halogen lamp and the like.

Figure 5:
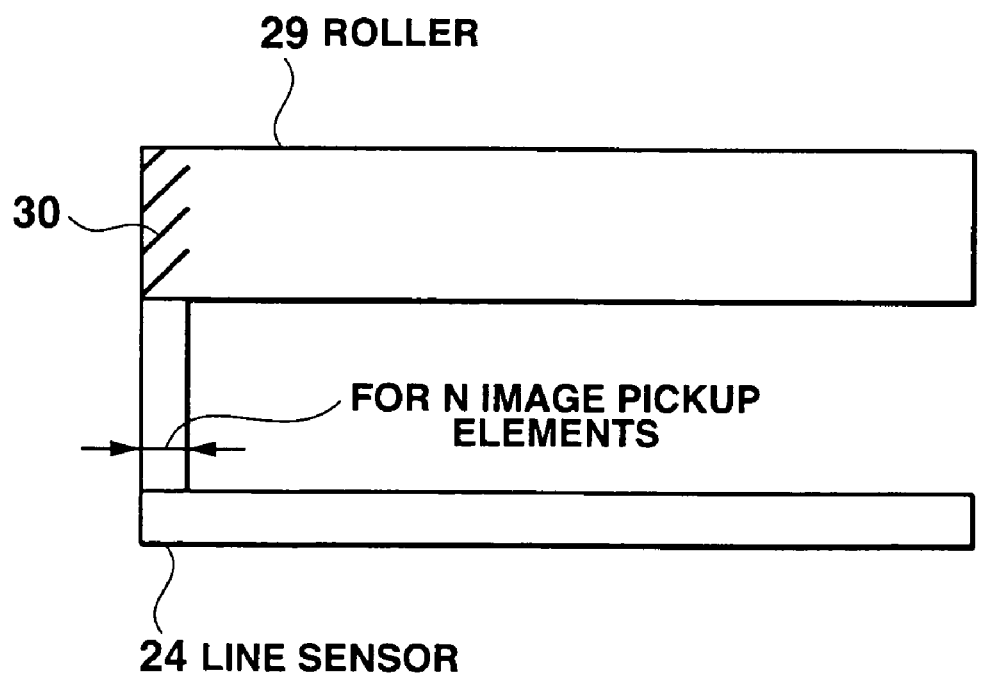
FIG. 5 is a diagram showing a correspondence between the printing pattern of the roller and image pickup elements of a line sensor in the fingerprint reading apparatus according to the embodiment of the present invention.

FIG. 5 shows a correspondence between the printing pattern 30 printed on the roller 29 and image pickup elements of the line sensor 24. The line sensor 24 has an image pickup range corresponding to the whole length of the roller 29. The number (N) of image pickup elements corresponding to the printing pattern 30 has been known and they are used for various processes described later.

Here are specific numeric values. When the diameter of the roller 29 is 7 mm and the resolution of the line sensor 24 is 600 dpi, the printing pattern 30 is formed at a segment angle of 45° and a segment interval of 40 dots (the length of forty image pickup elements of the line sensor 24, i.e., about 1.7 mm) and with a segment width of 2 dots (about 0.08 mm) and a diagonal line (about 2.5 mm in length) of two segments each having a length of 60 dots.

A fingerprint image reading operation performed by the fingerprint reading unit 20 will be described with reference to FIGS. 6 to 9.

The fingerprint reading unit 20 reads image data continuously from the line sensor 24 20000 times per second irrespective of the rotation of the roller 29 or the angle of the rotation. The image data includes the printing pattern 30 printed on the roller 29 as well as a fingerprint image (see FIG. 12).

The CPU 10 detects an amount of rotation of the roller 29 based on the amount of shift of black pixels (segments) included in the image data read by the line sensor 24, and stores image data necessary for forming a fingerprint image as fingerprint image data.

Figure 6:
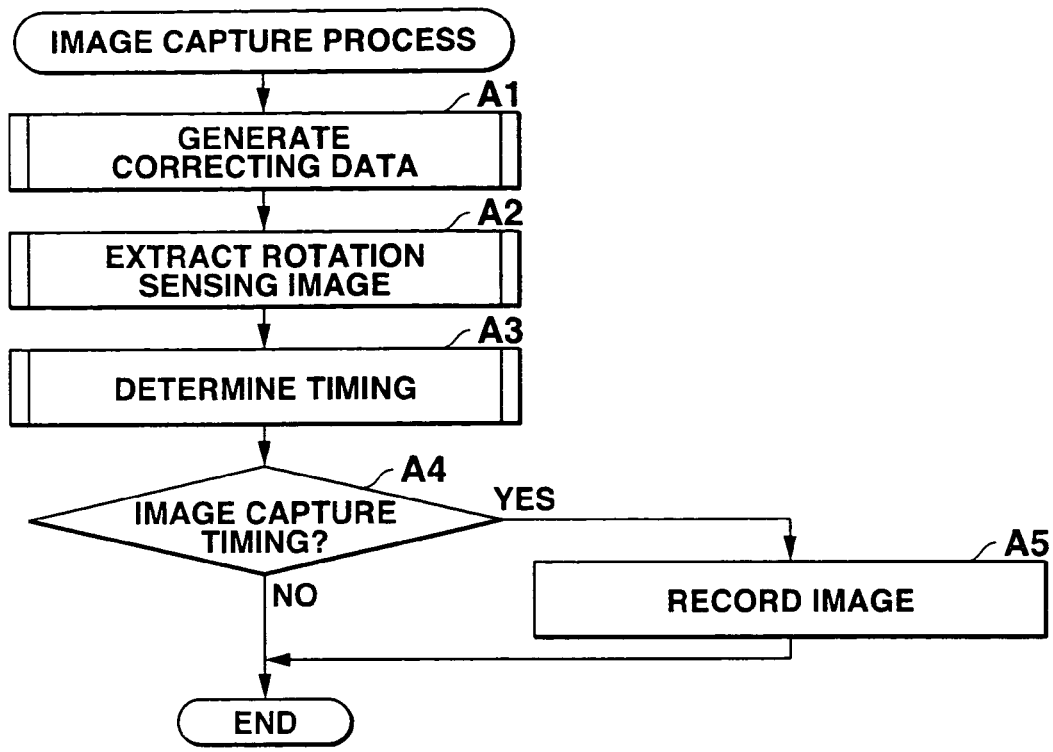
FIG. 6 is a main flowchart of an image capture process performed by the fingerprint reading apparatus according to the embodiment of the present invention.

FIG. 6 is a main flowchart of the entire process performed each time the line sensor 24 captures image data.

When image data of one line is read out of the line sensor 24, the CPU 10 generates correcting data (step A1). The correcting data is a pixel value representing black and white pixels based on which a rotation sensing image is recognized. The CPU 10 extracts a rotation sensing image using the correcting data (step A2). The CPU 10 determines image capture timing based on the amount of shift of the rotation sensing image (step A3) and then determines whether the image data is necessary for forming a fingerprint image (step A4). If now is the image capture timing, the image data of one line is captured as an image for forming a fingerprint (step A5).

There now follows a detailed description of each of the steps.

Figure 7:
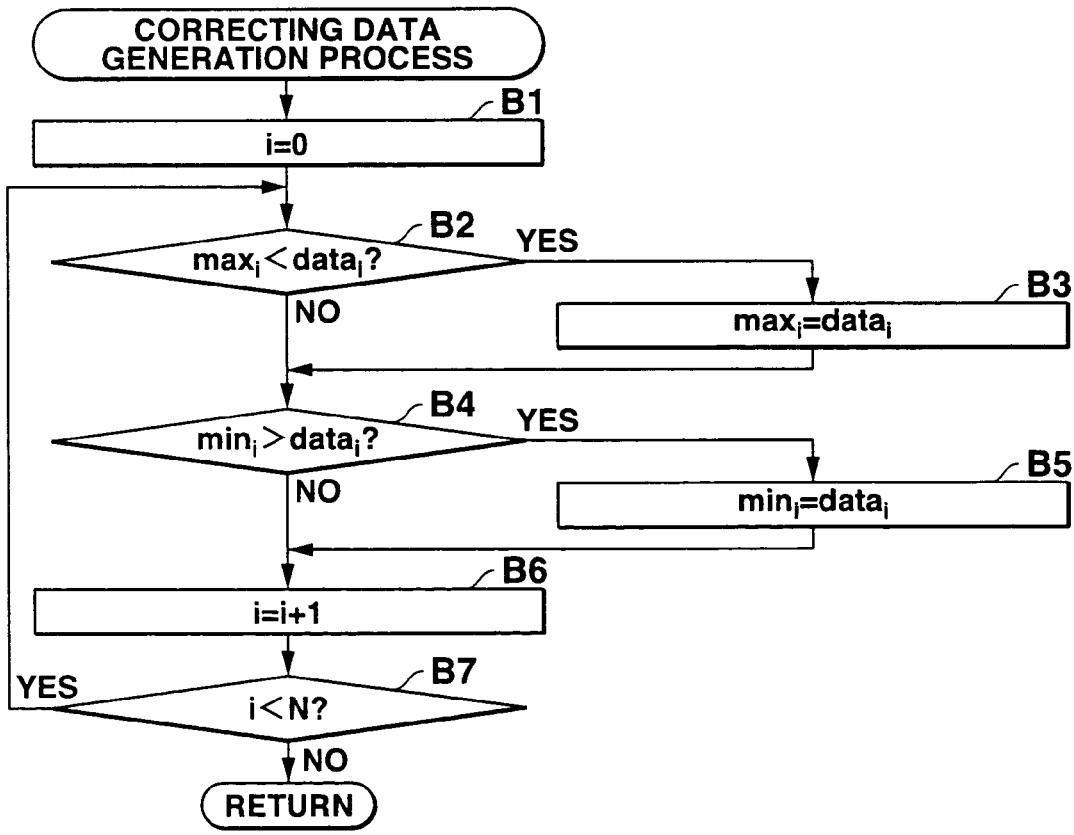
FIG. 7 is a flowchart of a correction data generation process in the image capture process performed by the fingerprint reading apparatus according to the embodiment of the present invention.

FIG. 7 is a flowchart showing a correcting data generation process in detail.

Of the pixel values of pixels that each image pickup element has read so far, the maximum value is recorded as a white reference value and the minimum value is recorded as a black reference value. These values are recorded as correcting data. As the roller 29 rotates, the image pickup element captures data (maximum and minimum values) that are considered to be white and black reference values.

Assume here that the number of image pickup elements used for reading a rotation sensing image is N, the maximum and minimum values of pixels that each image pickup element has read so far are $\{max_i|0 \leq i \leq n-1\}$, $\{min_i|0 \leq i \leq N-1\}$, respectively, and data that each image pickup element newly reads is $\{data_i|0 \leq i \leq N-1\}$.

When the CPU 10 reads pixels (pixel values) from the printing pattern 30 read by the line sensor, it initializes i to 0 (i=0) (step B1). The CPU 10 compares the maximum pixel value $max_i$ that the i-th image pickup element has read so far and the currently-noted pixel value $data_i$ (step B2). If $max_i < data_i$, the pixel value $data_i$ is updated to a new maximum value $max_i$ (step B3).

The CPU 10 also compares the minimum pixel value $min_i$ that the i-th image pickup element has read so far and the currently-noted pixel value $data_i$ (step B4). If $min_i > data_i$, the currently-noted pixel value $data_i$ is updated to a new minimum value $min_i$ (step B5).

The CPU 10 updates i to i+1 (i=i+1) (step B6). If i<N and all image pickup elements have not yet completed their operation for the printing pattern 30 (step B8), the CPU confirms whether the maximum and minimum values $max_i$ and $min_i$ should be updated by the pixel value $data_i$ read by the next i-th image pickup element in the same manner as described above.

The above process is carried out for the pixel values read by the image pickup elements 0 to N−1.

Figure 8:
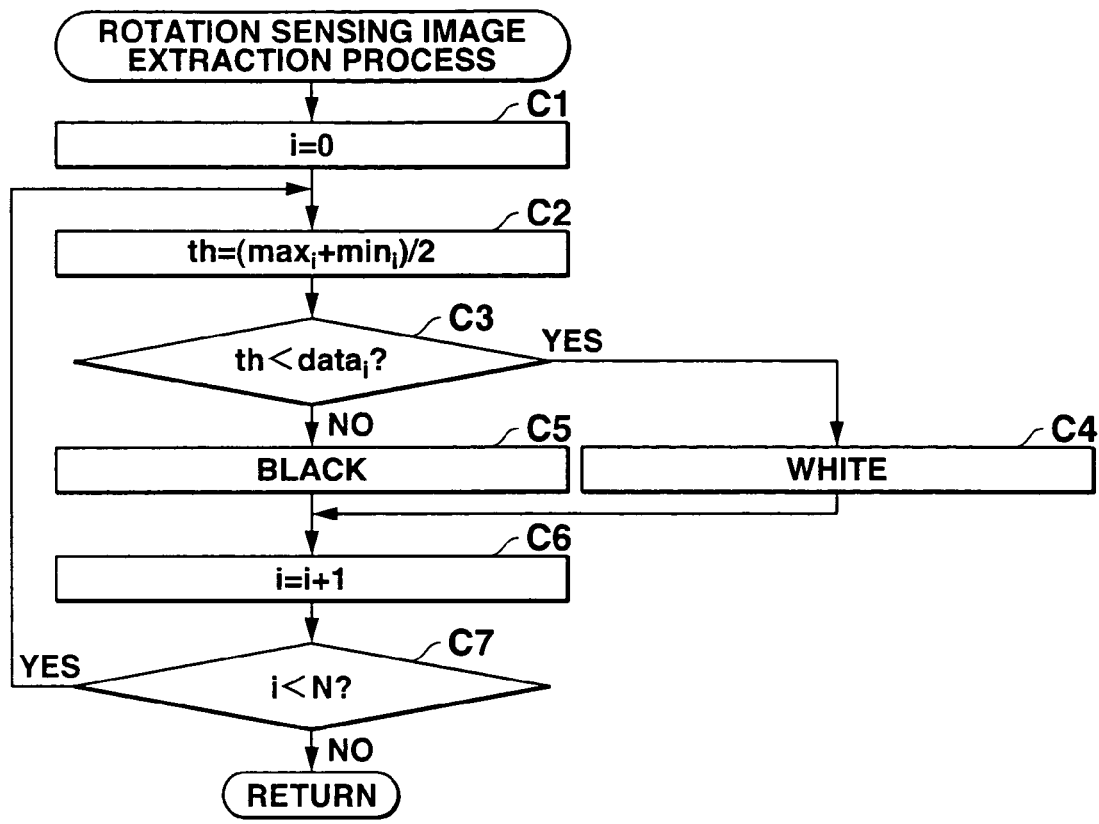
FIG. 8 is a flowchart of a rotation sensing image extraction process in the image capture process in the fingerprint reading apparatus according to the embodiment of the present invention.

FIG. 8 is a flowchart showing a rotation sensing image extraction process in detail.

In this process, the CPU 10 determines whether pixel data (pixel value) read by each image pickup element is black or white. This determination can be achieved on the basis of a threshold value that is obtained from the maximum and minimum values of the pixel data that the image pickup element has read so far. The image determined as black is processed as a rotation sensing image.

In this embodiment, the CPU 10 determines whether each pixel is black or white by considering an average of the maximum and minimum values to be a threshold value.

First, the CPU 10 initializes i to zero (i=0) (step C1). It calculates the sum of the maximum and minimum values $max_i$ and $min_i$ that the i-th image pickup element has so far read and considers half the sum to be a threshold value th (step C2). It compares the threshold value with the i-th pixel value $data_i$ (step C3). If $th < data_i$ (YES in step C3), the CPU 10 determines the pixel as white (step C4). If $th \geq data_i$ (NO in step C3), the CPU 10 determines the pixel as black (step C5).

Then, the CPU 10 updates i to i+1 (step C6). If i<N and each image pickup element has not yet completed its operation for the rotation sensing image (step C7), the CPU 10 determines whether the pixel value $data_i$ read by the next i-th image pickup element is black or white in the same manner as described above.

The above process is carried out for the pixel values read by the image pickup elements 0 to N−1. The CPU 10 can thus determine whether each pixel is black or white based on the average of the maximum and minimum values that have been so far read by each image pickup element. The black pixel can be extracted as a rotation sensing image.

Figure 9:
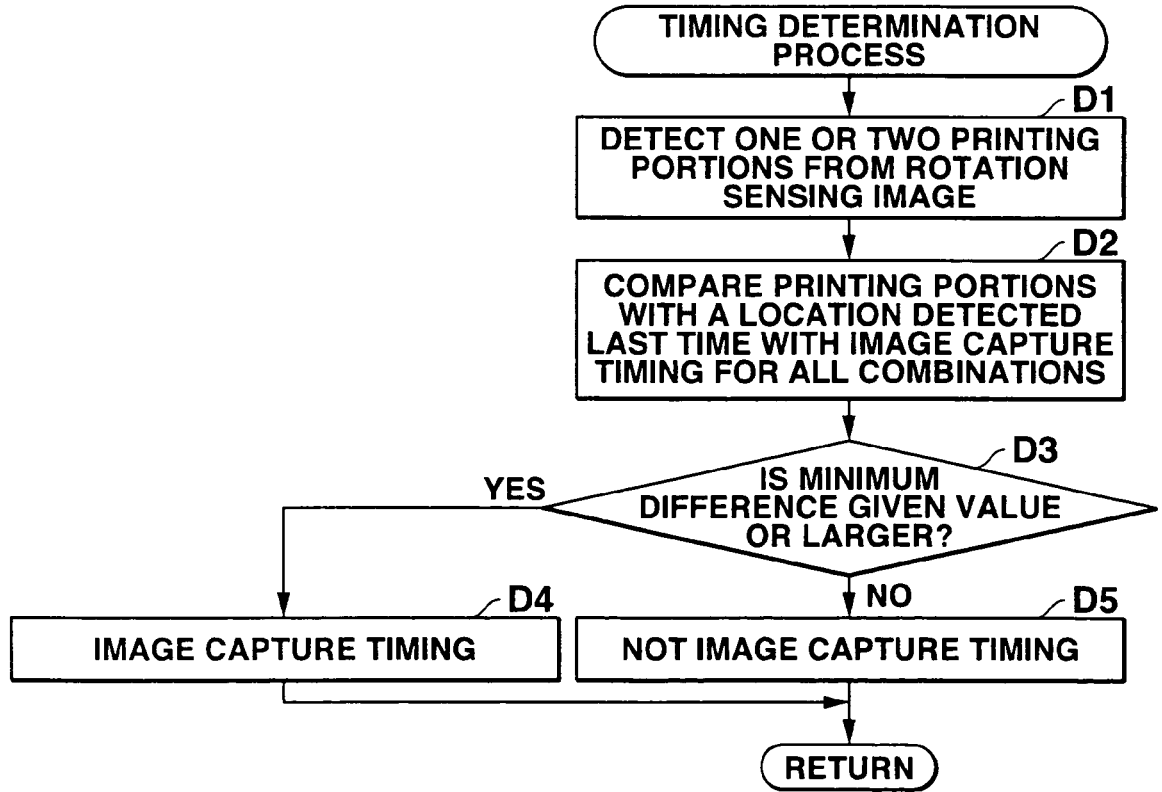
FIG. 9 is a flowchart of an image capture timing determination process in the fingerprint reading apparatus according to the embodiment of the present invention.
Figure 12A:
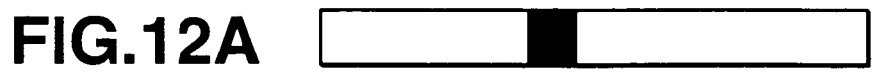
FIGS. 12A to 12D are illustrations of movement of a printing portion in a rotation sensing image in the fingerprint reading apparatus according to the embodiment of the present invention.
Figure 12B:
Figure 12C:
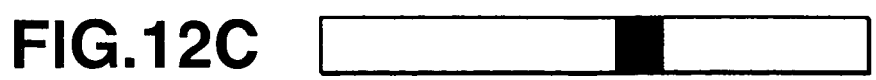
Figure 12D:
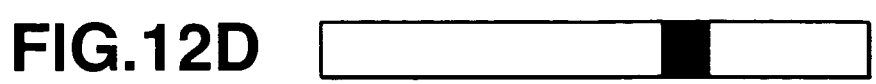

FIG. 9 is a flowchart showing a timing determination process in detail.

First, the CPU 10 senses one or two printing portions (black pixels) corresponding to segments of printing patterns 30 from the image determined as black by the rotation sensing image extraction process (step D1).

The CPU 10 compares a location of the sensed printing portion with that of the printing portion sensed last time with image capture timing (step D2). If the printing portions are separated at more than a given distance, the CPU 10 determines that now is image capture timing.

Since the printed segments (black portions) have a width, the line sensor 24 senses black portions of a plurality of pixels. In this case, the CPU 10 compares the middle of a row of black pixels or one end of the row as a printing portion. If there are a plurality of printing portions sensed last time with the image capture timing and those sensed this time, the printing portions are compared for all combinations of the printing portions.

FIG. 10 is a developed, plane view of the printing pattern 30 of the roller 29. The line sensor 24 reads an image in parallel to the rotation axis of the roller 29, or in the horizontal direction in FIG. 10. The segments (oblique lines) for forming the printing pattern 30 are arranged such that their adjacent segments overlap in a range defined by broken lines a and b in FIG. 10. The line sensor 24 can sense one or two portions of the printing pattern 30 by a single operation.

FIG. 11A shows a rotation sensing image that is read with the last image capture timing. Two printing portions a1 and a2 are sensed from the image. If another two printing portions b1 and b2 are sensed at this time as shown in FIG. 11B, the CPU 10 compares printing portions for each of four combinations a1 and b1, a1 and b2, a2 and b1, and a2 and b2.

Even though the line sensor 24 reads one end of a segment, it is to read an adjacent segment at once. Though the reading accuracy of the one end of the segment is low, the distance of printing portions is determined by all combinations of printing portions and thus the rotation of the roller 29 can stably be sensed on the basis of printing portions corresponding to the adjacent segment that is read with high precision.

If the minimum distance of all the combinations of printing portions is a given value or larger and the shift of the printing portions is confirmed (YES in step D3), the CPU 10 determines that now is image capture timing (step D4). In other words when the roller 29 is rotated with a subject pressed thereon and a new portion of the subject shifts to a reading position of the line sensor 24, the image read by the line sensor this time is captured as a fingerprint image. If the minimum distance is not larger than a given value (NO in step D3), the CPU 10 determines that now is not image capture timing (step D5).

In the above configuration, the diameter of the roller 29 is 7 mm, the resolution of the line sensor 24 is 600 dpi, the angle of each segment is 45°, the interval of segments is 40 dots, the width of each segment is 2 dots, and the length of each diagonal line is 60 dots. The amount of shift of a printing portion, which corresponds to image capture timing, can be set at one dot (0.04 mm).

If the CPU 10 determines the image capture timing through the image capture timing determination process (step E6), it records the image read by the line sensor 24 as a fingerprint image.

If the CPU 10 determines that now is not image capture timing, it abandons the image read by the line sensor 24.

The CPU 10 can determine image capture timing based on the shift of the locations of printing portions corresponding to the segments of the printing pattern 30 that is a rotation sensing image and generate a fingerprint image. Since the rotation sensing image is corrected in response to variations in outside light and light source, image capture timing can be determined with stability.

The segments of the printing pattern 30 are printed in parallel with each other at a given angle with respect to the rotation axis of the roller 29. The read portions of the printed segments shift right or left according to the direction in which the roller 29 rotates. In other words, the rotating direction of the roller 29 can be sensed by the direction in which the portions of the segments shift.

In the printing pattern 30 shown in FIG. 10, a user moves his or her finger in the direction A (toward the user) as shown in FIG. 3 and the roller 29 rotates in the direction B accordingly. The printing portion shifts in the left direction from that of the previously read rotation sensing image. If the user moves his or her finger away from him or her and the roller 29 rotates, the printing portion shifts in the right direction from that of the previously read rotation sensing image as shown in FIGS. 12A to 12D.

The CPU 10 can detect a direction in which the roller 19 rotates and determine whether an image is read from the lower part of a fingerprint or the upper part thereof (fingertip). The CPU 10 can record an image read with read timing in sequence from the upper or lower part of the fingerprint and generate a fingerprint image in a given direction (e.g., the fingertip is set upward). If the CPU 10 determines that an image is read from the lower part of the fingerprint, it can reverse the fingerprint 180 degrees after it reads all the images recorded in sequence.

As described above, the maximum and minimum values of the pixel values that have so far read are recorded for each of the image pickup elements of the line sensor 24, and the average of these values is considered to be a reference value. Since the CPU 10 recognizes a rotation sensing image based on the reference value, it can determine image capture timing with stability even though the image pickup elements vary in precision and the outside light and light source change. The segments of the printing pattern 30 printed on the roller 29 are arranged to overlap each other when the line sensor 24 captures an image. Even though one end of a single segment is a reading position of the line sensor 24, the line sensor 24 reads an image halfway in another segment; therefore, image capture timing can stably be determined without decreasing in precision.

The above printing pattern 30 is obtained by printing black segments on a white background. However, a portion other than the black segments can be printed. White segments can be printed on a black background and, in this case, they have only to be processed in the same manner as done for the black segments.

Figure 13A:
FIGS. 13A and 13B are diagrams showing another example of the printing pattern in the fingerprint reading apparatus according to the embodiment of the present invention.
Figure 13B:
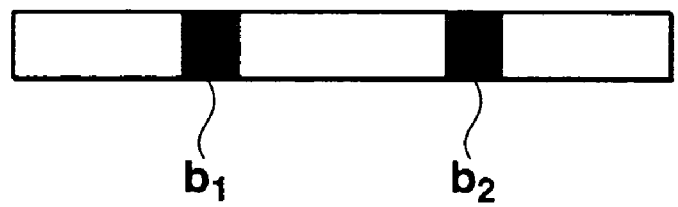

The segments of the printing pattern 30 are thickened to read a rotation sensing image as shown in FIG. 13A and sense edge portions where white changes to black or black changes to white as shown in FIG. 13B. Image capture timing can thus be determined according to variations in locations of the edge portions.

Figure 14:
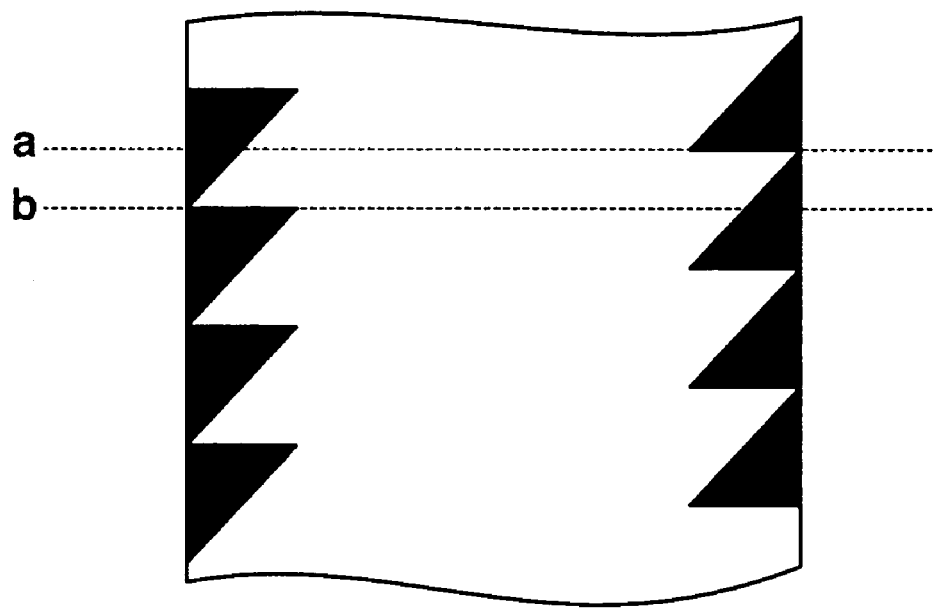
FIG. 14 is a diagram showing another example of the printing pattern in the fingerprint reading apparatus according to the embodiment of the present invention.

A saw-tooth pattern (isosceles triangles of the same shape are arranged adjacent to each other in the same direction) can be printed on either end of the roller 29 as shown in FIG. 14. The pattern is printed such that when the side of a triangle (which is parallel to the reading direction) at one end of the roller 29 is a reading position, the slant side of a triangle at the other end thereof becomes a reading position. In reading position a in FIG. 14, for example, the side of a triangle at the right end of the roller 29 becomes a reading position, which will probably decrease in precision. The slant side of a triangle at the left end of the roller 29 and thus the rotation of the roller 29 can be sensed with precision in accordance with variations in the position of the slant side.

The printing pattern 30 is printed on the roller 29. However, the surface of the roller 29 can be scratched and deformed to form a pattern, some materials can be adhered to the surface, or the surface can be melted. Any pattern will be formed on the surface of the roller 29 if the position of the image read by the image sensor 24 can be detected.

The image reading timing determination process using a printing pattern has been described so far. There now follows descriptions of a process of adjusting a pixel value when a fingerprint image is captured.

Figure 15:
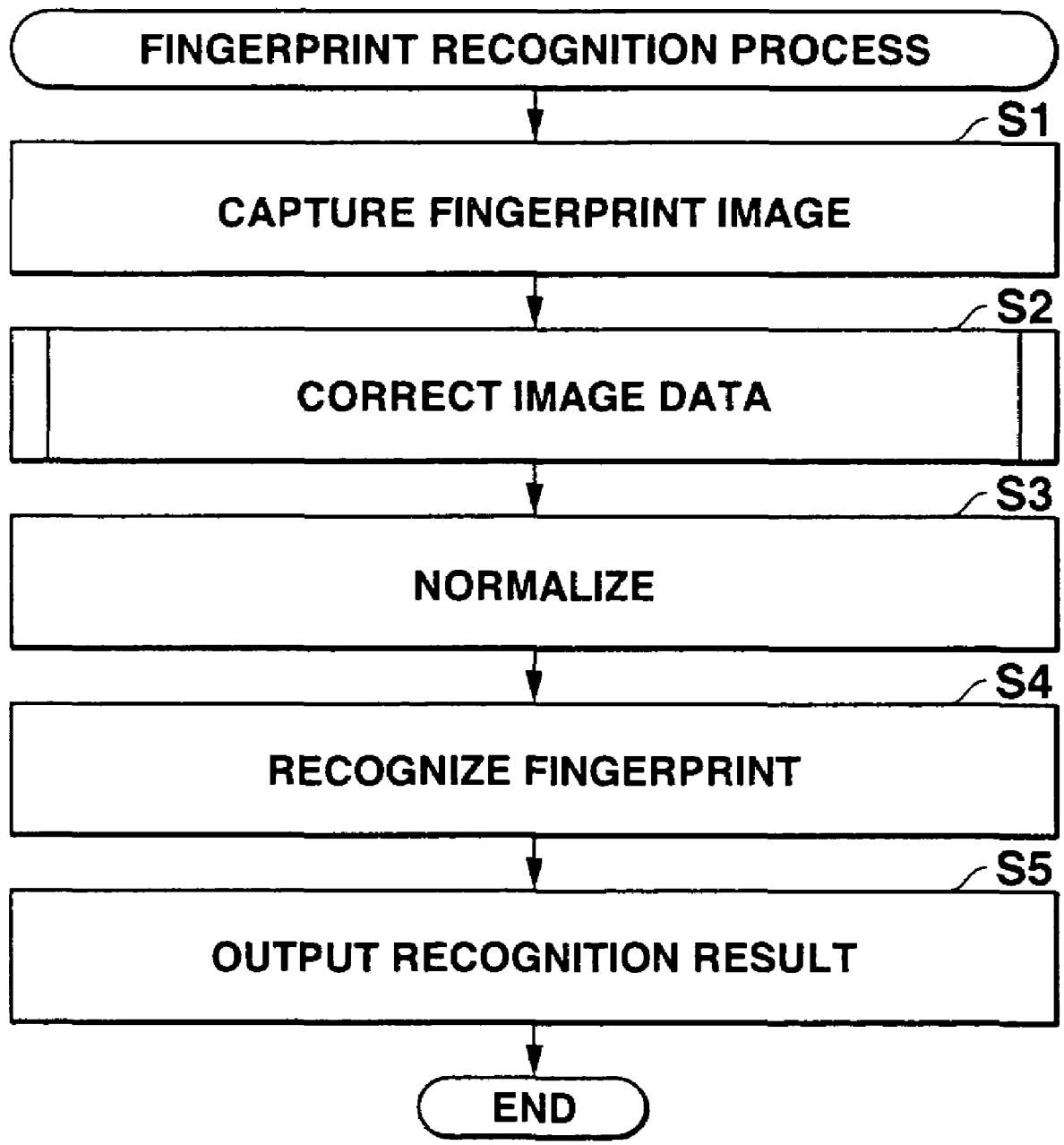
FIG. 15 is a flowchart illustrating a fingerprint recognition process performed by the fingerprint reading apparatus according to the embodiment of the present invention.

FIG. 15 is a flowchart illustrating a fingerprint recognition process of a mobile phone.

When the CPU 10 receives an instruction to perform a fingerprint recognition process from, e.g., the key unit 19, it executes a fingerprint recognition program to start the process. The CPU 10 then performs a fingerprint image reading process to read a fingerprint image to be recognized through the fingerprint reading unit 20 (step S1).

FIGS. 16A and 16B illustrate an example of how to move a finger when the fingerprint reading unit 20 reads a fingerprint image.

In FIG. 16A, a user's fingertip touches with a reading portion on the roller 29 and in this condition the roller 29 rotates and moves in a given direction (which is perpendicular to the rotation axis of the roller 29). In FIG. 16B, the fingertip moves toward the user. The user rotates the roller 29 while moving his or her fingertip. The line sensor 24, which is arranged in the roller 29 in parallel to the rotation axis of the roller 29, can scan a fingerprint portion of the fingertip.

The A/D conversion circuit 28 converts an image signal output from the line sensor 24 into digital data (fingerprint image data). The RAM 41 stores the fingerprint image data through the fingerprint reading unit 20. The fingerprint image data has a multilevel pixel value (e.g., 0 to 255). The fingerprint image data read by the unit 20 by optical scanning may include bias and variations in the pixel values under the influence of variations in the image pickup elements of the line sensor 24 and variations in the CELFOC lens (lens optical system) 22.

In order to correct the above bias and variations, the CPU 10 corrects the fingerprint image data read by the fingerprint reading unit 20 (step S2). The CPU 10 corrects the respective pixel values of the fingerprint image data.

Figure 19:
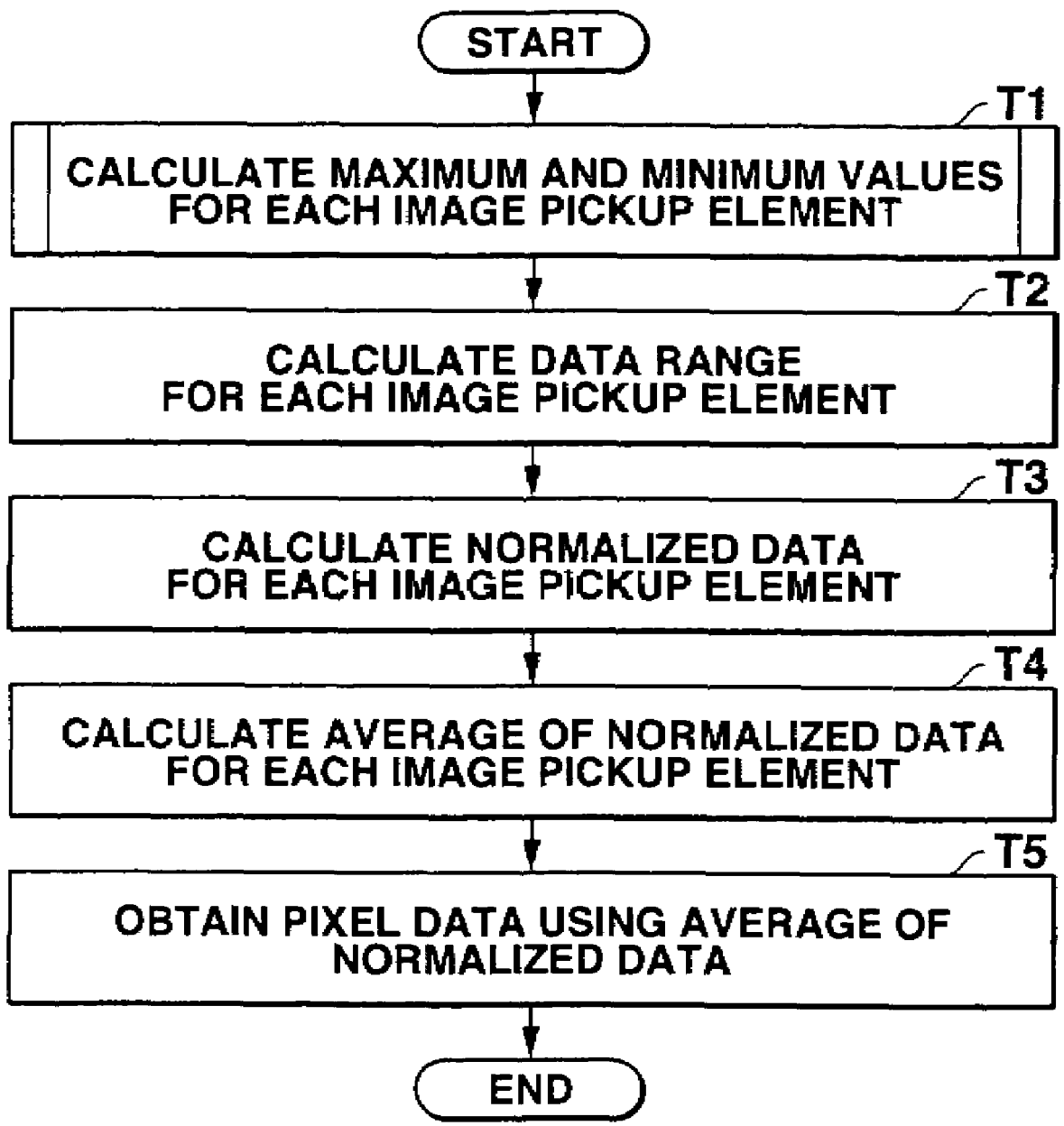
FIG. 19 is a flowchart illustrating in detail an image data correcting process in the fingerprint reading apparatus according to the embodiment of the present invention.

FIG. 19 is a flowchart showing an image data correcting process in detail.

Figure 17:
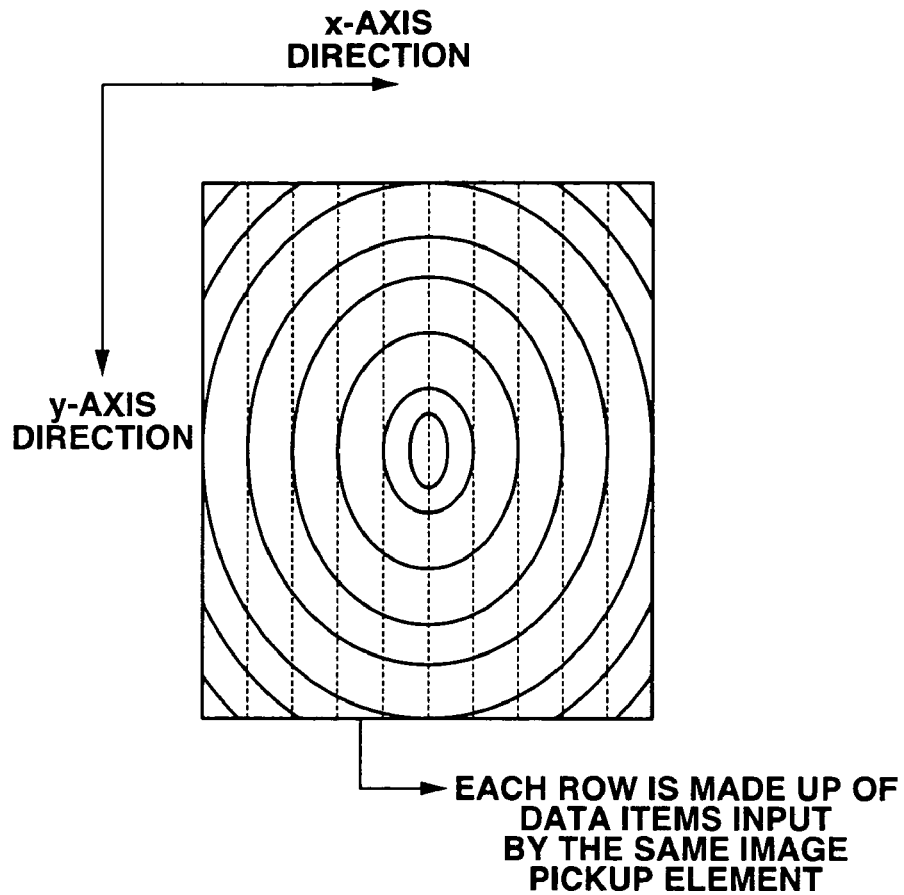
FIG. 17 is a diagram of an example of fingerprint image data read by a line sensor of the fingerprint reading apparatus according to the embodiment of the present invention.

The fingerprint image data read by the line sensor 24 includes a plurality of rows of data items, corresponding to each of the image pickup elements of the line sensor 24, that are arranged in the y-axis direction as shown in FIG. 17. The rows of data items are similar to one another in property. A fingerprint is made up of ridges and valleys and has nearly a uniform pattern. The data items of the respective rows do not widely differ in average or property (e.g., ratio of the number of pixels having each pixel value to the total number of pixels). The CPU 10 thus corrects the pixel values of the fingerprint image data using its property as will be described below.

Figure 18:
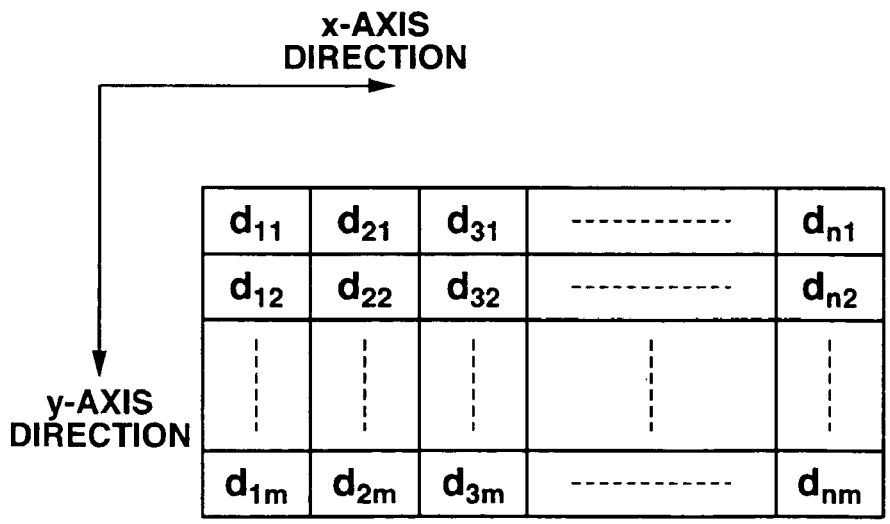
FIG. 18 is a diagram of an arrangement of pixels (pixel values) of fingerprint image data read by each image pickup element of a line sensor in the fingerprint reading apparatus according to the embodiment of the present invention.

First, the CPU 10 detects the maximum pixel value $max_i$ (first pixel value) and minimum pixel value $min_i$ (second pixel value) from image data read by each of the image pickup elements (step T1). FIG. 18 shows the pixels (pixel values) of image data D read by each of the image pickup elements.

$D=\{d_{ij}|i=1 \ldots n, j=1 \ldots m\}$. The maximum pixel value $max_i$ and minimum pixel value $min_i$ are given by the following equations (1) and (2):

$$max_i = MAX(d_{ij}|j=1 \ldots m), 1 \leq i \leq n \quad (1)$$

$$min_i = MIN(d_{ij}|j=1 \ldots m), 1 \leq i \leq n \quad (2)$$

where MAX( ) and MIN( ) are functions for obtaining the maximum and minimum pixel values.

Then, the CPU 10 calculates the width of data for each image pickup element, or the range between the maximum and minimum pixel values obtained in step T1, by the following equation (3) (step T2):

$$range_i = max_i - min_i, 1 \leq i \leq n \quad (3).$$

The CPU 10 calculates normalized data $d'_{ij}$ by the following equation (4) (step T3). The normalized data $d'_{ij}$ represents the ratio of pixel value $d_{ij}$ to pixel value range $range_i$ for the pixel captured by each of the image pickup elements of the line sensor 24.

$d'_{ij} = (d_{ij} - min_i)/range_i;$ $$1 \leq i \leq n, 1 \leq j \leq m \quad (4)$$

The CPU 10 calculates an average of normalized data $d'_{ij}$ by the following equation (5) (step T4):

$$ave_i = \frac{1}{m}\sum_{j=1}^{m} d'_{ij}; 1 \leq i \leq n \quad (5)$$

The CPU 10 obtains pixel data using the average of the normalized data $d'_{ij}$ (step T5). More specifically, the CPU 10 corrects a pixel value of each pixel of image data read by each of the image pickup element based on the average ($ave_i$) of normalized data $d'_{ij}$ calculated in step T4 and the pixel value (depth) of the pixel, by the following equation (6):

$$d''_{ij} = d'_{ij} \times \frac{depth}{2 \times ave_i}; 1 \leq i \leq n, 1 \leq j \leq m \quad (6)$$

where depth is the maximum pixel value of one pixel (e.g., 255 if one pixel is 8 bits).

When a pixel value is obtained by the proportional calculation of the above equation (6), it may exceed the maximum or minimum pixel value of one pixel. In this case, a clipping operation is performed to adjust the pixel value so as to fall within a range of the pixel value of one pixel.

The CPU 10 normalizes the fingerprint image data corrected by the image data correcting process to align its slope and size with those of the registered fingerprint image data of the original data (step S3).

The CPU 10 compares the normalized fingerprint image data with the registered fingerprint image data by the fingerprint comparing process (step S4). Since a fingerprint image to be compared in the stage precedent to the fingerprint comparing process is corrected, satisfactory comparing results can be expected.

The CPU 10 displays the results (OK, NG) of the fingerprint comparing process on, e.g., the display unit 18 (step S5).

Performing the above image data correcting process, the CPU 10 can correct the fingerprint image data read by the line sensor 24 to eliminate an influence based on variations in the image pickup elements and the CELFOC lens (lens optical system) 22. Since no data need to be prepared for adjustment in advance, no pre-scanning is required for image data correction. Since an image is corrected in response to variations in environment such as outside light when the image is read, fingerprint comparing results can always be obtained with stability regardless of the environment.

There now follows an explanation as to modifications (1) and (2) to the above embodiment.

Modification (1)

If, for example, dust is attached to the surface of the roller 29 when a fingerprint image is read, the dust will have a pixel value different from the normal pixel value of a fingerprint and thus the pixel value may correspond to the maximum or minimum pixel value. No fingerprint image can be accurately corrected due to the influence of the pixel value of the dust. In the corrected fingerprint image, the row of data items corresponding to the dust differs from the other rows in pixel value, with the result that a pattern such as a stripe (or a line) will be formed.

In the foregoing embodiment, the maximum and minimum pixel values are detected from the pixels captured by the image pickup elements of the line sensor 24. In the modification (1), however, the pixel values of pixels arranged in designated order are detected from the maximum and minimum pixel values. Image data can thus be corrected without any influence of pixels having incorrect pixel values due to dust or the like.

Figure 20:
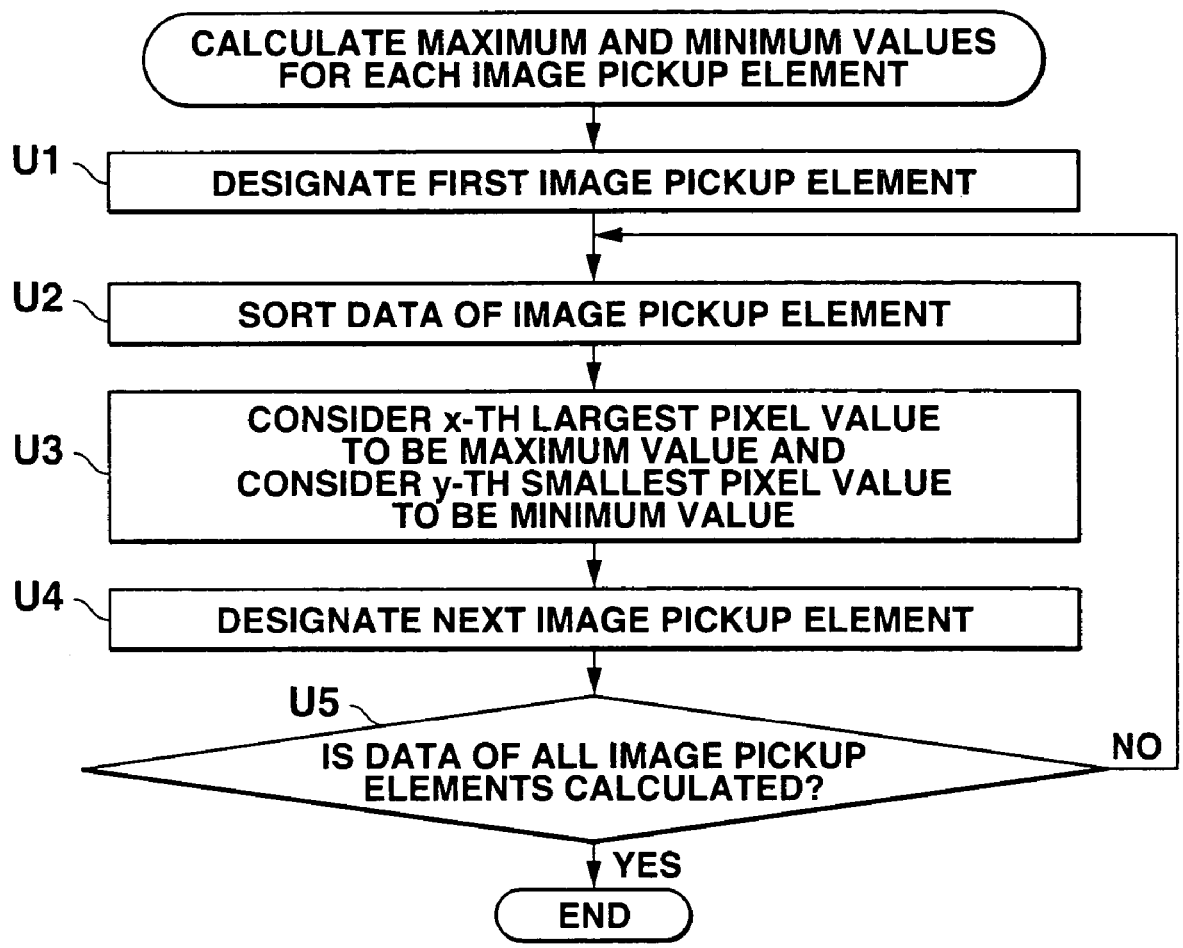
FIG. 20 is a flowchart of a first modification to step A1 in the flowchart shown in FIG. 19.

FIG. 20 is a flowchart showing in detail a step of the modification (1) which corresponds to the step T1 of the flowchart shown in FIG. 19. Since the other steps are the same as those of the image data correcting process shown in FIG. 19, their descriptions are omitted.

Assume in the modification (1) that the storage unit 12 stores a designated value indicating the order of pixels of image data captured by each image pickup element. The designated value can be recorded in the storage unit 12 in advance or through the key unit 19 by a user. For example, the storage unit 12 stores the how-manieth pixel (e.g., x) from a pixel with the maximum value in the pixels read by each image pickup element and the how-manieth pixel (e.g., y) from a pixel with the minimum value therein.

A group of pixels read by a first image pickup element of the line sensor 24 is designated (step U1). The pixels are sorted (in ascending or descending numeric order) based on their pixel values (step U2).

The x-th largest pixel value is detected as the maximum pixel value for generating normalized data, while the y-th smallest pixel value is detected as the minimum pixel value for generating normalized data (step U3).

The next image pickup element for detecting the minimum and maximum values is designated (step U4). Similarly, the x-th largest pixel value and the y-th smallest pixel value are detected from the group of pixels read by the image pickup element (steps U5, U2 and U3).

Image data items read by each of the image pickup elements are sorted when their pixels have a pixel value $\{d_{ij}|i=1\ldots n, j=1\ldots m\}$. Of the data items $\{d_{ij}|j=1\ldots m\}$ captured by the i-th image pickup element, the image data item with the maximum pixel value is $sd_{i1}$ and the image data item with the second maximum pixel value is $sd_{i2}$. If these image data items sorted in descending order are represented as $\{sd_{ik}|k=1\ldots m\}$, the maximum and minimum values $\max_i$ and $\min_i$ for normalizing data for each image pickup element are calculated as follows.

$$\max_i = sd_{ix} \quad (7)$$

$$\min_i = sd_{i(m-y+1)} \quad (8)$$

According to the modification (1), even though there are pixels with a pixel value that is not normally obtained from a fingerprint image due to, for example, dust attached to the roller 29, they can be eliminated by obtaining the maximum and minimum values $\max_i$ and $\min_i$ of the range of the pixel value to normalize data. The influence of the dust can thus be eliminated to correct image data.

Modification (2)

In the above modification (1), the x-th and y-th pixel value from the maximum and minimum values are detected from the pixels read by each image pickup element. However, the maximum and minimum pixel values for generating normalized data can be obtained from a group of pixels with the maximum value to the designated-manieth pixel and a group of pixels with the minimum value to the designated-manieth pixel. Assume here that the average of the former group of pixels is the maximum value and that of the latter group of pixels is the minimum value.

Figure 21:
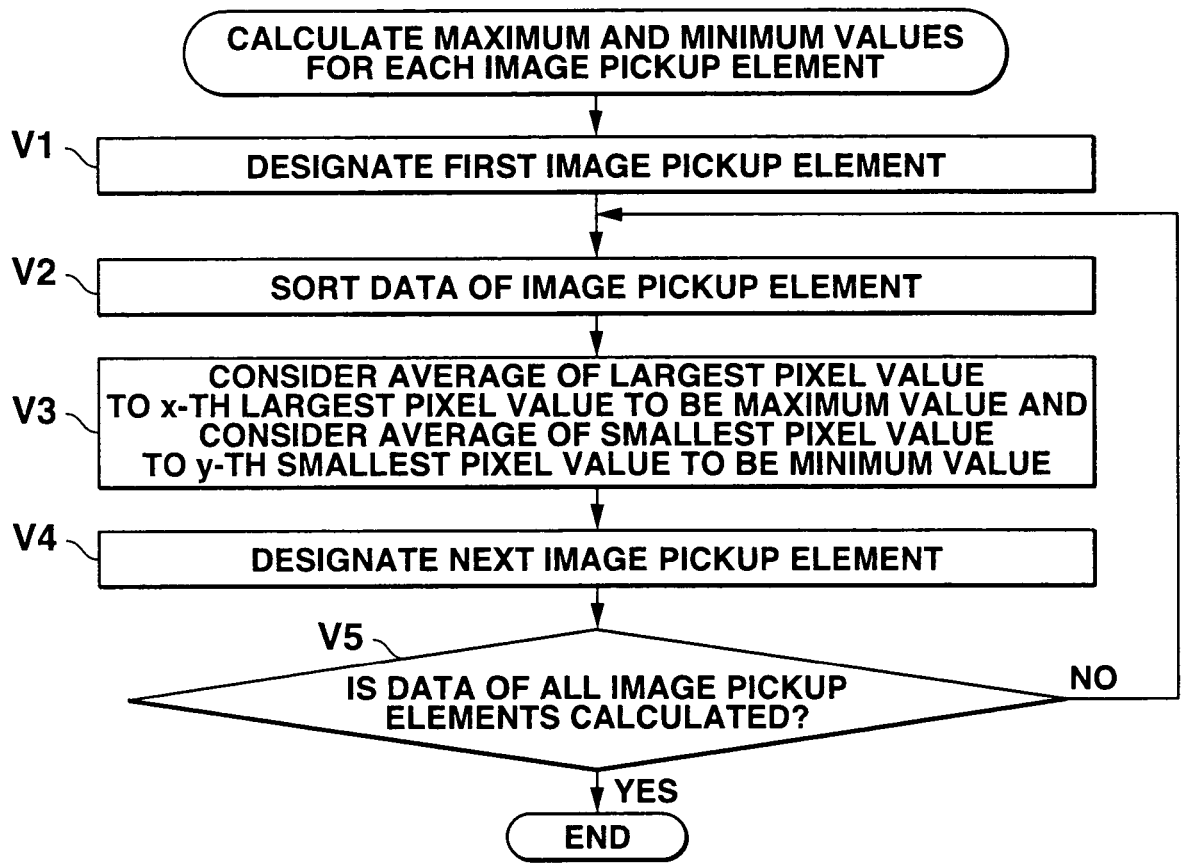
FIG. 21 is a flowchart of a second modification to step A1 in the flowchart shown in FIG. 19.

FIG. 21 is a flowchart showing in detail a step of the modification (2) which corresponds to the step T1 of the flowchart shown in FIG. 19. Since the other steps are the same as those of the image data correcting process shown in FIG. 19, their descriptions are omitted. Assume in the modification (2) that the storage unit 12 stores a designated value indicating the order of pixels of image data captured by each image pickup element, as in the modification (2).

A group of pixels read by a first image pickup element of the line sensor 24 is designated (step V1). The pixels are sorted (in ascending or descending numeric order) based on their pixel values (step V2).

The average of pixel values of a pixel with the maximum value to the x-th pixel is detected as the maximum pixel value for generating normalized data, while the average of pixel values of a pixel with the minimum value to the y-th pixel is detected as the minimum pixel value for generating normalized data (step V3).

The next image pickup element for detecting the maximum and minimum values is designated (step V4). Similarly, the average of pixel values of the pixel with the maximum value to the x-th pixel and that of pixel values of the pixel with the minimum value to the y-th pixel are detected from the group of pixels read by the image pickup element (steps U5, U2 and U3). These averages are considered to be the maximum and minimum values (steps V5, V2 and V3).

For example, the average of pixel values of the pixel with the maximum value to the x-th pixel and that of pixel values of the pixel with the minimum value to the y-th pixel are given by the following equations (9) and (10), respectively.

$$\max_i = \frac{1}{x}\sum_{j=1}^{x} sd_{ij}; \ 1 \leq i \leq n \quad (9)$$

$$mix_i = \frac{1}{y}\sum_{j=m-y+1}^{m} sd_{ij}; \ 1 \leq i \leq n \quad (10)$$

According to the modification (2), good results can stably be obtained by calculating the maximum and minimum pixel values. Fingerprint image data captured by each image pickup element includes an image portion corresponding to a number of ridges and valleys of a fingerprint. Of a set (group) of pixels having a pixel with the maximum or minimum pixel value through a designated-manieth pixel, there are a number of pixels whose pixel values are close to one another. Even though dust is attached to the roller 29, the influence of pixels corresponding to the dust can be lessened by obtaining the average of the group of pixels.

In the foregoing descriptions, the fingerprint image data reading apparatus is applied to mobile phones. It can be applied to other information devices or used alone.

In the foregoing descriptions, the fingerprint image data reading apparatus is used to read a fingerprint image. It can read image data such as a palm print pattern. The fingerprint reading unit 20 (line sensor 24) can read a palm print image if the pixel values of pixels of the palm print image, which are arranged in the y-axis direction, are similar to each other in average and maximum and minimum pixel values thereof between the image pickup elements of the unit 20 as in the case of the above fingerprint image.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A fingerprint image processing apparatus comprising:
   a line sensor including a plurality of image pickup elements;
   a pixel value detecting unit which detects a respective maximum value and a respective minimum value from fingerprint image data output from each of the image pickup elements;
   a pixel value range detecting unit which detects a pixel value range between the respective maximum value and the respective minimum value detected by the pixel value detecting unit for the fingerprint image data read by each of the image pickup elements;
   a normalized data generating unit which generates, for each pixel of the fingerprint image data, normalized data that indicates a ratio of a pixel value of the pixel to the pixel value range corresponding to the image pickup element which read the pixel;
   a normalized data average calculating unit which calculates averages, corresponding respectively to the image pickup elements, of the normalized data generated by the normalized data generating unit from the fingerprint image data read by the respective image pickup elements; and
   a pixel value correcting unit which corrects a pixel value of each of the pixels of the fingerprint image data based on: (i) the average calculated by the normalized data average calculating unit corresponding to the image pickup element which read the pixel, and (ii) a maximum possible pixel value of the pixels.

2. The apparatus according to claim 1, wherein the pixel value detecting unit comprises:
   a designated value recording unit which records a designated value that indicates an order of the pixel values of the pixels of the fingerprint image data output from the image pickup elements;
   a unit which determines, as the respective maximum value for the fingerprint image data from each of the image pickup elements, a pixel value of a pixel of the fingerprint image data output from the image pickup element that is an x-th largest pixel value recorded by the designated value recording unit, which is determined with reference to a maximum value detected from the fingerprint image data output from the image pickup element, and which determines, as the respective minimum value for the fingerprint image data from each of the image pickup elements, a pixel value of a pixel of the fingerprint image data output from the image pickup element that is a y-th smallest pixel value recorded by the designated value recording unit, which is determined with reference to a minimum value detected from the fingerprint image data output from the image pickup element.

3. The apparatus according to claim 1, wherein the pixel value detecting unit includes:
   a designated value recording unit which records a designated value that indicates an order of the pixel values of the pixels of the fingerprint image data output from the image pickup elements;
   a unit which determines, as the respective maximum value for the fingerprint image data from each of the image pickup elements, an average of pixel values from a maximum pixel value detected from the fingerprint image data output from the image pickup element to an x-th pixel value recorded by the designated value recording unit, which is determined with reference to a minimum value detected from the fingerprint image data output from the image pickup element, and which determines, as the respective minimum value for the fingerprint image data from each of the image pickup elements, an average of pixel values from a minimum pixel value detected from the fingerprint image data output from the image pickup element to a y-th pixel value recorded by the designated value recording unit, which is determined with reference to a minimum value detected from the fingerprint image data output from the image pickup element.

4. The apparatus according to claim 1, further comprising a hollow transparent roller which is rotatably mounted at a main body of the image processing apparatus, and wherein the line sensor is fixed in the roller.

5. The apparatus according to claim 4, wherein the line sensor reads a fingerprint image of a finger that is in contact with the roller to obtain the fingerprint image data.

6. A method of processing fingerprint image data, which is captured by a line sensor that includes a plurality of image pickup elements, and each pixel of the fingerprint image data having a multilevel pixel value, the method comprising:
   detecting a respective maximum value and a respective minimum pixel value from the fingerprint image data captured by each of the image pickup elements of the line sensor;
   detecting a pixel value range between the respective maximum value and the respective minimum value for the fingerprint image data captured by each of the image pickup elements;
   generating, for each pixel of the fingerprint image data, normalized data that indicates a ratio of a pixel value of the pixel to the pixel value range corresponding to the image pickup element which read the pixel;
   calculating averages of the normalized data corresponding respectively to the image pickup elements; and
   correcting a pixel value of each of the pixels of the fingerprint image data based on: (i) the average corresponding to the image pickup element which read the pixel, and (ii) a maximum possible pixel value of each of the pixels.

7. The method according to claim 6, wherein the pixel value detecting includes:
   recording a designated value that indicates an order of the pixel values of the pixels of the fingerprint image data output from the image pickup elements;
   determining, as the respective maximum value for the fingerprint image data from each of the image pickup elements, a pixel value of a pixel of the fingerprint image data output from the image pickup element that is an x-th largest pixel value indicated by the designated value, which is determined with reference to a maximum value detected from the fingerprint image data output from the image pickup element; and determining, as the respective minimum value for the fingerprint image data from each of the image pickup elements, a pixel value of a pixel of the fingerprint image data output from the image pickup element that is a y-th smallest pixel indicated by the designated value, which is determined with reference to a minimum value detected from the fingerprint image data output from the image pickup element.

8. The method according to claim 6, wherein the pixel value detecting includes:

recording a designated value that indicates an order of the pixel values of the pixels of the fingerprint image data output from the image pickup elements;

determining, as the respective maximum value for the fingerprint image data from each of the image pickup elements, an average of pixel values from a maximum pixel value detected from the fingerprint image data output from the image pickup element to an x-th pixel value indicated by the designated value, which is determined with reference to a maximum value detected from the fingerprint image data output from the image pickup element; and determining, as the respective minimum value for the fingerprint image data from each of the image pickup elements, an average of pixel values from a minimum pixel value detected from the fingerprint image data output from the image pickup element to a y-th pixel value indicated by the designated value, which is determined with reference to a minimum value detected from the fingerprint image data output from the image pickup element.

9. The method according to claim 6, further comprising capturing a fingerprint image by the line sensor to obtain the fingerprint image data.

* * * * *